(12) United States Patent
Nitz et al.

(10) Patent No.: US 9,035,102 B2
(45) Date of Patent: May 19, 2015

(54) HYDROLYSIS OF THE RESIDUES OBTAINED IN THE PRODUCTION OF ISOPHORONE TO RECOVER ISOPHORONE AND ACETONE

(71) Applicants: Joerg-Joachim Nitz, Essen (DE); Stephan Kohlstruk, Duelmen (DE); Robert Jansen, Bottrop (DE); Matthias Orschel, Muenster (DE); Andreas Merkel, Recklinghausen (DE); Michael Demming, Duelmen (DE); Matthias Mendorf, Dortmund (DE); Jens Doering, Dortmund (DE); Axel Hengstermann, Senden (DE); Andreas Hoff, Eslohe (DE); Anja Mueller, Dortmund (DE)

(72) Inventors: Joerg-Joachim Nitz, Essen (DE); Stephan Kohlstruk, Duelmen (DE); Robert Jansen, Bottrop (DE); Matthias Orschel, Muenster (DE); Andreas Merkel, Recklinghausen (DE); Michael Demming, Duelmen (DE); Matthias Mendorf, Dortmund (DE); Jens Doering, Dortmund (DE); Axel Hengstermann, Senden (DE); Andreas Hoff, Eslohe (DE); Anja Mueller, Dortmund (DE)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 14/454,786

(22) Filed: Aug. 8, 2014

(65) Prior Publication Data
US 2015/0045585 A1  Feb. 12, 2015

(30) Foreign Application Priority Data

Aug. 12, 2013 (DE) .................. 10 2013 215 874

(51) Int. Cl.
*C07C 45/42* (2006.01)
*C07C 45/74* (2006.01)
*C07C 45/82* (2006.01)
*C07C 49/603* (2006.01)

(52) U.S. Cl.
CPC ................ *C07C 45/74* (2013.01); *C07C 45/82* (2013.01); *C07C 49/603* (2013.01)

(58) Field of Classification Search
CPC ............................... C07C 45/74; C07C 45/85
USPC ........................................ 568/344, 347, 353
See application file for complete search history.

(56) References Cited

U.S. PATENT DOCUMENTS

| 3,981,918 A | 9/1976 | Walton et al. |
|---|---|---|
| 4,059,632 A | 11/1977 | Cane et al. |
| 2013/0253226 A1 | 9/2013 | Galle et al. |
| 2013/0261343 A1 | 10/2013 | Orschel et al. |
| 2014/0107379 A1 | 4/2014 | Orschel et al. |

FOREIGN PATENT DOCUMENTS

| DE | 26 45 281 A1 | 4/1944 |
|---|---|---|
| DE | 25 20 681 A1 | 11/1975 |
| DE | 10 2010 062 587 A1 | 6/2012 |
| DE | 10 2011 075 777 A1 | 11/2012 |

OTHER PUBLICATIONS

Extended European Search Report issued Dec. 9, 2014 in Patent Application No. 14177090.9 (with English Translation of Category of Cited Documents).

*Primary Examiner* — Sikarl Witherspoon
(74) *Attorney, Agent, or Firm* — Oblon, McClelland, Maier & Neustadt, L.L.P.

(57) ABSTRACT

A process for preparing isophorone (3,5,5-trimethyl-2-cyclohexen-1-one) is provided wherein distillation vapors from the work-up of product fractions are recycled to earlier stages of operation of the process.

34 Claims, No Drawings

HYDROLYSIS OF THE RESIDUES OBTAINED IN THE PRODUCTION OF ISOPHORONE TO RECOVER ISOPHORONE AND ACETONE

CROSS REFERENCE TO RELATED APPLICATIONS

This application claims priority to German Application No. 102013215874.2, filed Aug. 12, 2013, the disclosure of which is incorporated herein by reference in its entirety.

BACKGROUND OF THE INVENTION

The invention relates to a process for preparing isophorone (3,5,5-trimethyl-2-cyclohexen-1-one).

The invention especially relates to an extension of the process for preparing isophorone for improved raw material utilization. This involves rehydrolysing the organic residues obtained in order to recycle the materials of value which form into the process. A "material of value" is understood to mean, as well as acetone and isophorone, especially also the intermediates phorone, mesityl oxide and diacetone alcohol.

Isophorone is used inter alia as a high-boiling solvent in the coatings industry, printing inks industry, adhesives industry and crop protection industry. In addition, isophorone may be processed further, for example to give isophoronenitrile, isophoronediamine, isophorone diisocyanate or ketoisophorone.

Isophorone is the trimeric condensation product of acetone. Isophorone is prepared via a catalysed aldol condensation of acetone.

The reaction in the liquid phase is described in the patent literature virtually exclusively under alkaline conditions at elevated temperatures and high pressures.

The patent documents of Hibernia Chemie (DE 10 95 818, DE 11 44 269, DE 12 05 525, DE 11 65 018) from the 1960s describe not only the use of a monophasic reactant/catalyst mixture with low alkali concentrations but also workup by means of a hydrolysis column. According to these documents, isophorone is prepared in a pressure reactor by condensation of acetone in the liquid phase by means of amounts of alkali (NaOH or KOH) of less than 1% as a catalyst and using amounts of water of less than 20% at temperatures of 150-250° C. The two phases which form in the reaction are emulsified both by a suitable reaction regime (reactor construction, pulse generator) and by the use of an emulsifier in order to achieve good contact between catalyst and the reactants (DE 10 95 818).

In addition, DE 12 05 525 describes the workup of by-products, called overcondensates. At 120-300° C., the hydrolysis of the overcondensates takes place with an aqueous alkali solution in what is called a pressure distillation column with constant removal of the acetone formed.

Pure isophorone is recovered from isophorone-containing condensation products by a removal of the low boilers by distillation under the same pressure at which the condensation is performed and by a further workup of the overcondensates still existing by distillation under reduced pressure (DE 11 44 269).

According to the application by BP Chemicals, use of potassium hydroxide solution (KOH) instead of the otherwise customary catalyst, sodium hydroxide solution (NaOH), can enhance the isophorone yield by up to 7% with constant selectivity (DE 25 20 681).

It has also been stated that the product quality of the isophorone can be increased by discharging colouring substances from the reaction column in a sidestream, and purifying this stream by distillation and acidic reaction (DE 26 45 281).

There also exist applications regarding isophorone preparation from Daicel Chemical Industries (JP 8245485, JP 8245486) from the 1990s. These state that reduction of the water concentration in the reactant stream, and also recycling of the aqueous alkali phase after phase separation into the hydrolysis section of the reactive distillation, can enhance the isophorone conversion.

WO 2012/076314 discloses a process for preparing isophorone by catalysed aldol condensations with acetone as a reactant, workup of the reaction product, hydrolysis of the stream of value and separation into an organic fraction and an aqueous fraction, recovery of isophorone from the organic fraction, distillative workup of the aqueous fraction and passage of the vapours from the top of the distillative workup apparatus onward into the hydrolysis apparatus.

In this process, the redissociation of the overcondensates in the hydrolysis does not take place completely because of the equilibrium positions of the reactions that take place, and so overcondensates that are still hydrolysable, which can be converted to materials of value by an additional hydrolysis, are present in the residues obtained at the end of the isophorone purification. In the existing process according to WO 2012/076314, these residues are sent to incineration.

The synthesis of isophorone forms a whole series of by-products. These are, for example, diacetone alcohol, mesityl oxide, phorone, mesitylene and a series of higher condensation products (overcondensates) of acetone (e.g. xylitones and isoxylitones). For this reason, the achievement of high yields and selectivities for isophorone is difficult to attain.

The technical problem addressed by this invention was therefore to find a process which enables an increase in the economic viability of isophorone preparation.

SUMMARY OF THE INVENTION

This and other objects are achieved by the present invention, the first embodiment of which includes a process for preparing isophorone, comprising:

A) catalysed aldol condensation with acetone as a reactant;

B) workup of the reaction product, the workup in stage B) being effected so as to give three fractions:

a) a fraction composed of unconverted acetone, water and low boilers, which is condensed and then recycled into the reactor for reaction;

b) a fraction in which colouring substances in particular are enriched, this fraction being purified further and the materials of value present being recycled into the process;

c) a fraction composed of isophorone, more highly condensed products and water and catalyst, called material of value stream, this fraction subsequently being subjected to a first hydrolysis in which by-products are converted partly or fully to isophorone, acetone and other products of value;

C) wherein the worked-up fraction c) is subjected to a phase separation into an essentially organic fraction d) and an essentially aqueous fraction e);

D) distillative workup of the aqueous fraction e) and passage of the vapours from the top of the distillative workup apparatus onward into the hydrolysis apparatus of A);

E) purification of the organic fraction d) to give the following three fractions:

i) residue,
ii) pure isophorone,
iii) remaining low boilers;

F) hydrolysis of the residue i) in a second hydrolysis and recycling of the products of value formed into the process.

DESCRIPTION OF THE PREFERRED EMBODIMENTS

As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted. Where a numerical limit or range is stated, the endpoints are included. Also, all values and subranges within a numerical limit or range are specifically included as if explicitly written out.

It has been found that, surprisingly, the hydrolysis of the residues formed in the isophorone preparation proceeds more efficiently when a further hydrolysis is performed after the removal of isophorone. The hydrolysis of c) and i) as according to the present invention leads to a further conversion of the hydrolysable constituents of the residue that are still present. This leads to an increase in the yield of isophorone with respect to the amount of acetone used, and to an increase in the economic viability of isophorone preparation.

The inventive process may be performed continuously, batchwise or semicontinuously. However, it is preferably performed continuously.

Isophorone 1 is prepared via catalysed aldol condensations with acetone as the reactant. In the first step, two acetone molecules react via the diacetone alcohol intermediate with elimination of water to form mesityl oxide. In a further reaction the mesityl oxide reacts with a further acetone, again with elimination of water, to form isophorone.

Isophorone is thus the reaction product of a condensation of three molecules of acetone with the elimination of two molecules of water.

As a consequence of the chemical similarity of the reactant used (acetone) and the intermediates/products formed, the isophorone synthesis does not proceed particularly selectively. Due to the multitude of competing aldol condensation reactions, under reaction conditions, not only is the desired isophorone target molecule obtained, but also a whole series of unwanted (higher) condensation products (e.g. xylitones and isoxylitones), and also further secondary components (e.g. mesitylene).

The isophorone synthesis comprises a complex reaction network; the selectivity is highly dependent on the conversion. In order to minimize the formation of unwanted (higher) condensation products, the acetone conversion has to be limited. Particularly in the gas phase reaction, the catalyst used can be deactivated by coking residues which form. It has been found that the reaction mixture which forms may be worked up by the inventive process in a particularly economically viable and ecologically favourable manner to give isophorone.

The condensation reaction of acetone to isophorone (reaction) may preferably be conducted in a catalysed liquid phase reaction. Alternatively, isophorone may also be prepared by a gas phase reaction, or by reaction in supercritical acetone.

For the performance of the reaction in accordance with the process according to the invention in the liquid phase, the acetone is converted to isophorone within the reactor used by catalytic reaction at temperatures in the range from 100 to 250° C., preferably 150-250° C. and more preferably 180-250° C., and a pressure range of 5 to 50 bar, preferably 10-50 bar and more preferably of 20-50 bar, it being possible to combine the values specified as desired.

For the performance of the reaction in accordance with the process according to the invention in the gas phase, the acetone is converted to isophorone within the reactor used by catalytic reaction at temperatures in the range from 100 to 400° C. and preferably 200-400° C.

For the performance of the reaction in accordance with the process according to the invention in the supercritical range, the acetone is converted to isophorone within the reactor used by catalytic reaction at temperatures in the range from 250 to 350° C. and a pressure range of 50 to 200 bar.

The catalytic reaction may be conducted with conventionally known catalysts, and the catalyst may be either a homogeneous or a heterogeneous catalyst. In the liquid phase, preference may be given to using a homogeneous catalyst, and in the gas phase preference may be given to using a heterogeneous catalyst. For the reaction in the supercritical range, it is possible to use either homogeneous or heterogeneous catalysts.

In the preferred reaction in the liquid phase, isophorone may be prepared in the presence of a homogeneous catalyst with amounts of alkali (NaOH or KOH) of <1% by weight, preferably of <0.5% by weight, more preferably <0.2% by weight. More preferably, the catalyst used is NaOH in amounts of 0.015 to 0.05% by weight. The water concentration used may be determined by factors including the recycle streams of the workup processes; it should, based on the total amount of liquid, be <40%, preferably <30%.

The reaction may be performed in conventional reactors, including, for example, tubular reactors, stirred tanks, stirred tank cascades, fixed bed reactors, pressure distillation reactors or reactive distillations, microstructured reactors, loop reactors, etc., or in combinations of any desired reactors. The choice of reactors is not restricted to the selection mentioned.

The term "pressure distillation reactor" according to the present invention includes all apparatuses in which a reactive distillation may be performed. The reactive distillation has been described in the specialist literature, for example in Ullmann's Encyclopedia of Industrial Chemistry (M. Sakuth, D. Reusch, R. Janowsky: Reactive Distillation ©2008 Wiley-VCH Verlag GmbH & Co KGaA, Weinheim, DOI: 10.1002/14356007.c22_c01.pub2). According to the present invention and in the literature cited, all standard processes and apparatuses for reactive distillation are described. According to the present invention, the term "reactive distillation column" includes all embodiments of reactive distillation as conventionally known.

In a preferred version, the reaction may be conducted in reactive distillation columns, tubular reactors or fixed bed reactors. Particular preference may be given to tubular reactors.

After performing the reaction, the reaction mixture is worked up in stage 2 and separated into the individual components. These are, as well as isophorone, what are called low boilers, for example acetone, diacetone alcohol and mesityl oxide, and also a series of higher condensation products (overcondensates) of acetone (e.g. xylitones and isoxylitones) and water, with or without catalyst. The separation may be performed in full or in part.

The removal of the individual fractions may be conducted by all separation methods, including, for example, distillation, flash evaporation, crystallization, extraction, sorption, permeation, phase separation or combinations of the above, continuously or batchwise, in one or more stages. Preference may be given to separation by distillation in one or more apparatuses.

The distillation may be conducted spatially separately from the isophorone synthesis (reaction) or take place in one apparatus. Preferably, the individual fractions are removed by a reactive distillation, preferably in a reactive distillation column.

Particular preference may be given to conducting the removal spatially separately from the isophorone synthesis (reaction) in a reactive distillation column with a sidestream withdrawal.

According to the invention, the removal is effected so as to give three fractions:

a) A fraction composed of unconverted acetone, water and low boilers, for example diacetone alcohol and mesityl oxide, which is condensed and then recycled into the reactor for reaction.

b) A fraction in which coloring substances in particular are enriched. This fraction is purified further and the materials of value present are recycled into the process.

c) A fraction composed particularly of isophorone, more highly condensed products and water, with or without catalyst, called stream of value. This fraction is subsequently subjected to a first hydrolysis.

In one preferred embodiment, fraction a) is withdrawn as a vapor stream comprising essentially acetone, water and low boilers, essentially diacetone alcohol and mesityl oxide, condensed and added again to the reactor with the acetone, water and optionally catalyst feedstocks.

Fraction b) may be withdrawn as a sidestream of the distillation column, preferably of a reactive distillation column, optionally neutralized and worked up further. In the workup, it is possible to use all standard separation methods, for example distillation, flash evaporation, crystallization, extraction, sorption, permeation, phase separation, or combinations of the above. The purification can be performed continuously or batchwise, in one or more stages. The purification may preferably be achieved by distillation. The purification is more preferably achieved by a combination of neutralization or extraction and subsequent distillation, preferably in a reactive distillation column. The worked-up phase is preferably conducted into the hydrolysis with the products of value composed of isophorone and high boilers, with or without catalyst. Any further phase obtained, composed of products of value essentially comprising acetone, diacetone alcohol and mesityl oxide, is preferably recycled into the reaction. Any residues obtained may be sent to thermal utilization.

Fraction c) is subjected to a first hydrolysis. The object of the first hydrolysis is to convert by-products partly or fully to isophorone, acetone and other products of value. The hydrolysis may be performed in all standard reactors, which have already been described above, or distillation columns or combinations of the two. Preference may be given to performing the hydrolysis by a reactive distillation, in which the low boilers formed, essentially comprising acetone, diacetone alcohol and mesityl oxide, are removed directly from the hydrolysis zone and recycled into the reaction, and are thus no longer available for side reactions in the hydrolysis.

Most preferably, the first hydrolysis of fraction c) may be conducted in an apparatus, by a reactive distillation, preferably in a reactive distillation column, with simultaneous separation of the reaction mixture into fractions a) to c), such that the products formed are correspondingly separated at the same time and fraction c) is hydrolysed.

Optionally, the first hydrolysis and the distillative removal can also take place in one apparatus with the isophorone synthesis (reaction).

The first hydrolysis may be performed in all mixing ratios of the organic components with water, with or without catalyst. The water concentration in the hydrolysis may be 0.1-99.9% by weight, preferably 30-90% by weight. In the case of homogeneous catalysis, the catalyst used in the hydrolysis may preferably be that which is also used in the reaction section. Preference may be given to catalyst concentrations of 0.001-10% by weight, more preferably of 0.05-1% by weight. The pressure in the hydrolysis reactor may be 1-200 bar, preferably 20-60 bar; more preferably, the hydrolysis may be conducted at least at the pressure which also exists in the isophorone synthesis reaction. The hydrolysis temperature may be 100-300° C., preferably 210-260° C. More preferably in the case of use of a reactive distillation column, a temperature or temperature profile may be established according to the boiling temperatures in the bottoms and at the individual separation or reaction stages.

The first hydrolysis can be performed in one or more apparatuses, in one stage or multiple stages.

The fraction c) thus worked up is subsequently removed from the first hydrolysis reactor or reactive distillation column, cooled and subjected to a phase separation.

The phase separation is conducted to give an organic fraction d) and an aqueous fraction e), which, in the case of homogeneous catalysis, also comprises the catalyst. It is possible to use conventional phase separation vessels with and without internals. The phase separation may be conducted at a temperature between 0-200° C., preferably at 0-100° C. and more preferably at 20-70° C., and a pressure of 1-150 bar and preferably 20-60 bar, more preferably at the pressure which also exists in the hydrolysis.

The essentially organic fraction d) comprising the isophorone target product may optionally be neutralized and purified by conventional methods, so as to obtain isophorone with the desired purity and color stability. Conventional separation methods, for example distillation, flash evaporation, crystallization, extraction, sorption, permeation, phase separation or combinations of the above may be employed. The purification may be conducted continuously or batchwise, in one or more stages, under pressure or under reduced pressure.

The purification of the organic fraction d) may be conducted to give the following three fractions:

i) residue,
ii) pure isophorone,
iii) remaining low boilers.

The purification may preferably be achieved by distillation. The purification may preferably be achieved by a combination of neutralization or extraction and subsequent distillation.

The fraction i) residue is subjected to an additional hydrolysis (second hydrolysis).

The second hydrolysis may be conducted under the same conditions as the first hydrolysis previously described. The second hydrolysis can be performed in all mixing ratios of the organic components with water, with or without catalyst. The water concentration in the hydrolysis is 0.1-99.9% by weight, preferably 30-90% by weight. In the case of homogeneous catalysis, the catalyst used in the hydrolysis is preferably that which is also used in the reaction section. Preference is given to catalyst concentrations of 0.001-10% by weight, more preferably of 0.05-1% by weight. The pressure in the hydrolysis reactor is 1-200 bar, preferably 20-60 bar; the hydrolysis temperature is 100-300° C., preferably 210-260° C.

The second hydrolysis may be performed in one or more apparatuses, in one or more stages.

The second hydrolysis may be performed in all standard reactors, described above, or in distillation columns or combinations of the two, preferably in at least one reactive distillation column.

The products of value in the vapors which arise in the second hydrolysis of the residue i) are, as well as isophorone and acetone, further low boilers convertible to isophorone, especially diacetone alcohol, mesityl oxide and phorone. The products of value formed are subsequently recycled into the process and hence utilized physically. Preference is given to recycling into the first hydrolysis. Preference is given to passage of the vapors onward from the top of the second hydrolysis apparatus into the first hydrolysis apparatus. Particular preference is given to conducting the second hydrolysis in one stage in a reactive distillation column.

The hydrolysis of the residue i) gives rise to advantages compared to the process of WO 2012/076314. The residue i) which is supplied to the second hydrolysis contains virtually no isophorone; this leads to a more favourable position of the reaction equilibrium than in the hydrolysis of fraction c) (first hydrolysis), such that the hydrolysis can proceed to a greater extent.

At this point, the distillative workup of the aqueous fraction e) (wastewater cleaning) and conduction of the vapours from the top of the distillative workup apparatus into the first hydrolysis apparatus will be described in detail.

The essentially aqueous fraction e) is preferably supplied to a wastewater cleaning operation. Here, the water of reaction as the main constituent is separated, with or without the catalyst, from any organic components still dissolved, for example isophorone, acetone and more highly condensed products. The wastewater cleaning operation is described in detail in WO 2012/076314 and WO 2012/156187.

Preferably, the wastewater cleaning operation is conducted in the presence of an antifoam, which virtually completely prevents foam formation in the bottom of this wastewater column and hence achieves very good separation between the main water constituent and the organic components still dissolved, for example isophorone, acetone and other low boilers, and also higher-boiling products. Moreover, the fill height of the wastewater column can thus be determined exactly, and the wastewater column can be prevented both from overflowing and from running dry.

The wastewater cleaning operation may preferably be performed in one or more distillation columns. It is essential to the invention that the vapors of the wastewater column are passed directly into the apparatus in which the hydrolysis 1 takes place. This simultaneously solves several problems associated with conventionally known processes:

1) Since the vapors consist essentially of water, a necessary sufficiently high water concentration is established in the hydrolysis section, such that no additional fresh water need be introduced into the hydrolysis.

2) The organic components dissolved in fraction e) are recycled partially or completely into the process via the vapors of the wastewater column. This minimizes organic contamination in the wastewater and, since the contamination is essentially isophorone, increases the overall yield in the process. This novel connection of the wastewater column thus makes a significant contribution to the ecological and economic process regime.

3) Moreover, the necessary heat for the hydrolysis or the distillative separation of the reaction mixture is provided by the vapors; no separate heating is required.

The pressure in the wastewater column may be 1-200 bar, preferably 20-60 bar. Particular preference may be given to working at the system pressure which is established in the overall hydrolysis/wastewater column system when the vapors of the wastewater column are passed directly into the hydrolysis section of the reactive distillation. The temperature in the wastewater column corresponds to the boiling temperature of fraction e) under the pressure conditions. The preferred temperature of the vapors is 200-300° C.

There follows a detailed description of how the water from the bottom of the distillative workup of the aqueous fraction e) is subjected to a flash evaporation and the cleaned water formed is recycled into the process for preparing isophorone.

The wastewater obtained in the bottom of the wastewater column (stream f) can be cooled and discarded. Preferably, the wastewater f), however, is sent to a flash evaporation and thus separated further. The vapours g) of the flash evaporation stage, which consist essentially of pure water, may be condensed and recycled as water into the process, preferably into the reaction, for example for dilution of the catalyst used (in the case of homogeneous catalysis). This once again reduces the amount of wastewater. The flash evaporation may be performed in one or more stages, continuously or batchwise. The pressure in the flash evaporation is in any case below the pressure in the wastewater column. In the process according to the invention, preference may be given to the use of a flash evaporation.

All distillation and reaction steps in the process may be conducted in reactors or apparatuses with or without internals, for example dephlegmators, unordered internals or random packagings, ordered internals or structured packings, trays with or without forced flow.

All metallic materials which are in contact with the product and are used for the reaction, and the apparatuses produced from the metallic materials and the internals thereof, must be stable to alkalis. Depending on the risk, different stability requirements may exist. For the stabilities, not only the chemical and/or mechanical properties are of significance, but also the methods of manufacture employed and the assessment standards during the testing.

For the metallic materials, reference is made in some cases to the AD 2000-Merkblatt HP 0, 11.2008 edition (General Principles of Design, Manufacture and Associated Tests) and DIN EN 10020, 07.2000 edition (Determination and Classification of Grades of Steel). The material groups named therein are cited to specify the designations (e.g. "austenitic stainless steel"). If meaningful in a technical sense, the statements apply to all industrially available variants of the materials (for example forged variants, rolled variants and cast variants) with comparable stability to alkali corrosion.

a) For pressure-bearing components in contact with product, suitable materials may include:
Heat-resistant steels (e.g. material subgroups 5.1 to 5.4 and 6.1 to 6.4 according to AD 2000 HP 0)
Austenitic stainless steels (e.g. material subgroups 8.1 to 8.2 according to AD 2000 HP 0)
Ferrite-free austenitic stainless steels (e.g. material subgroups 8.1 to 8.2 according to AD 2000 HP 0)
Ferritic-austenitic stainless steels (e.g. material subgroups 10.1 to 10.2 according to AD 2000 HP 0)
Nickel and nickel alloys (e.g. material subgroups 41 to 46 according to AD 2000 HP 0)

It may also be possible to employ combinations of the abovementioned materials. In this case, the choice of materials is not restricted to the selection mentioned and also includes equivalent or higher-quality variants in terms of corrosion. Preference may be given to materials which, according to conventional knowledge, taking account of the stress conditions and risks, feature industrial stability to alkalis. It is not possible to dispense with heat treatments if this impermissibly alters the technical stability to alkalis.

b) For non-pressure-bearing components in contact with product, any materials suitable according to conventional wisdom may be employed, and include, for example:

All materials mentioned under a)
Unalloyed steels (e.g. material subgroups 1.1 to 1.2 according to AD 2000 HP 0)
Unalloyed steels and other alloyed steels (e.g. according to DIN EN 10020)

It may also be possible to employ combinations of the abovementioned materials. In this case, the choice of materials is not restricted to the selection mentioned and also includes equivalent or higher-quality variants in terms of corrosion. Preference may be given to materials which, according to conventional wisdom, taking account of the stress conditions and risks, feature sufficient stability to alkalis. For non-pressure-bearing components, it may be possible to accept temporary stabilities depending on the risk. It is not possible to dispense with heat treatments if this impermissibly alters the technical stability to alkalis.

c) The material properties are altered by suitable manufacturing processes which are described hereinafter according to the designations given in DIN 8580, 09.2003 edition (manufacturing processes—terms and definitions, division). The following manufacturing processes can be employed, for example, for the processing of the metallic materials:

Primary shaping (e.g. casting)
Reshaping (e.g. cold forming and hot forming)
Separating (e.g. machining with geometrically defined blade and machining with geometrically undefined blade)
Joining (e.g. fusion welding)
Coating (e.g. coating from the liquid state, melt dipping, plating, thermal spraying, sintering, electrocoating, chemical coating and coating from the gaseous and vaporous state)
Manufacturing processes which alter material properties (consolidation by reshaping, for example forging, rolling, blasting; heat treatment, for example tempering, recrystallization annealing, low-voltage annealing, normalization annealing; thermomechanical treatments, for example the combination of heat treatment and forming treatment; sintering and firing).

It is also possible to employ combinations of the abovementioned manufacturing processes. In this case, the choice of manufacturing processes is not restricted to the selection mentioned. Preference is given to processes which are conventionally known to ensure the required alkali stability of the respective materials and apparatuses.

d) The following tests on apparatuses and internals, and more particularly on the weld bonds thereof, for example, can be employed:

Magnet particle testing MT
Penetration testing PT
Radiographic testing RT
Ultrasound testing UT
Visual testing VT
Hardness testing HT
Alloy analysis Combinations of the abovementioned test methods are also possible. In this case, the choice of test methods is not restricted to the selection mentioned. Preference is given to test methods and assessment principles which, according to the prior art, contribute to ensuring the required alkali stability of the respective components.

Example (According to the Invention)

Isophorone was prepared by the steps as described in the description. Fraction d) was worked up by distillation. 0.12 kg of residue i) was obtained per kg of isophorone produced.

The residue i) from the workup was subjected to an additional hydrolysis 2.

The hydrolysis 2 was performed in a one-stage distillation apparatus by the principle of a reactive distillation. This apparatus consisted of a heated stirred vessel and two lines in order to pass steam and nitrogen into the vessel. There was also a connection in order to remove, condense and collect the vapors which formed. The experiment was conducted under the following conditions:

300 g of residue i) and 1500 g of water were initially charged in the reactor and heated while stirring (about 400 rpm). In the course of this, the nitrogen flow rate was set to 10 g/h and the plant pressure to 36 bar. After the reactor had been heated to 240° C., the 25% sodium hydroxide solution was injected into the reactor by means of the pressurized reservoir and the pressurized reservoir was purged with the 188 g of water. 23% by weight of materials of value were obtained from the residue i). The materials of value which form include acetone, isophorone, phorone, diacetone alcohol and mesityl oxide.

Comparison to the Preparation According to WO 2012/076314

By conducting the additional hydrolysis detailed above, it was thus possible to save 0.04 kg of acetone in the overall process according to stages 1-6 per kilogram of isophorone prepared. The yield of isophorone was increased by 3% by weight in the overall process according to stages 1-6.

The invention claimed is:

1. A process for preparing isophorone, comprising:
A) catalysed aldol condensation with acetone as a reactant;
B) workup of the reaction product,
the workup in stage B) being effected so as to give three fractions:
a) a fraction composed of unconverted acetone, water and low boilers, which is condensed and then recycled into the reactor for reaction;
b) a fraction in which colouring substances in particular are enriched, this fraction being purified further and the materials of value present being recycled into the process;
c) a fraction composed of isophorone, more highly condensed products and water and catalyst, called material of value stream, this fraction subsequently being subjected to a first hydrolysis in which by-products are converted partly or fully to isophorone, acetone and other products of value;
C) wherein the worked-up fraction c) is subjected to a phase separation into an essentially organic fraction d) and an essentially aqueous fraction e);
D) distillative workup of the aqueous fraction e) and passage of the vapours from the top of the distillative workup apparatus onward into the hydrolysis apparatus of A);
E) purification of the organic fraction d) to give the following three fractions:
i) residue,
ii) pure isophorone,
iii) remaining low boilers;
F) hydrolysis of the residue i) in a second hydrolysis and recycling of the products of value formed into the process.

2. The process for preparing isophorone according to claim 1, wherein water from the bottoms of the distillative workup D) of the aqueous fraction e) is subjected to a flash evaporation to obtain a purified water and the purified water is recycled into the process for preparing isophorone.

3. The process for preparing isophorone according to claim 1, wherein the reaction is conducted in a liquid phase, a temperature of the acetone condensation is from 100 to 250° C., and a pressure of the acetone condensation is from 5 to 50 bar.

4. The process for preparing isophorone according to claim 1, wherein the acetone condensation reaction is conducted in a gas phase, at a temperature of from 100 to 400° C.

5. The process for preparing isophorone according to claim 1, wherein the acetone condensation reaction is conducted in a supercritical range at a temperature of 250 to 350° C. and a pressure of 50 to 200 bar.

6. The process for preparing isophorone according to claim 1, wherein the catalyst for the aldol condensation is a homogeneous or heterogeneous catalyst.

7. The process for preparing isophorone according to claim 3, wherein the catalyst for the aldol condensation is a homogeneous catalyst.

8. The process for preparing isophorone according to claim 7, wherein the catalyst is an alkali and a content of the catalyst is from greater than 0 to less than 1% by weight of the reaction mixture.

9. The process for preparing isophorone according to claim 1, wherein the reaction is conducted in at least one reactor selected from the group consisting of a tubular reactor, a stirred tank, a stirred tank cascade, a fixed bed reactor, a reactive distillation column, a microstructured reactor and a loop reactor.

10. The process for preparing isophorone according to claim 9, wherein the reaction is conducted in a tubular reactor.

11. The process for preparing isophorone according to claim 1, wherein the work-up of the reaction mixture B) to obtain fractions a), b) and c) is performed by at least one separation method selected from the group consisting of distillation, flash evaporation, crystallization, extraction, sorption, permeation and phase separation, continuously or batchwise, in at least one stage.

12. The process for preparing isophorone according to claim 1, wherein the work-up of the reaction mixture B) to obtain fractions a), b) and c) is conducted spatially separately from the acetone condensation or is conducted by reactive distillation.

13. The process for preparing isophorone according to claim 12, wherein the work-up of the reaction mixture B) to obtain fractions a), b) and c) is conducted by reactive distillation, in a reactive distillation column, with a sidestream withdrawal.

14. The process for preparing isophorone according to claim 1, wherein fraction a) is withdrawn as a vapor stream comprising acetone, water, diacetone alcohol and mesityl oxide, condensed and the condensate added to the reaction mixture with the acetone, water and catalyst feedstocks.

15. The process for preparing isophorone according to claim 1, wherein fraction b) is withdrawn as a sidestream of a distillation column.

16. The process for preparing isophorone according to claim 1, wherein fraction b) is purified by a combination of neutralization or extraction and subsequent distillation in a reactive distillation column.

17. The process for preparing isophorone according to claim 1, wherein the materials of value of fraction b) are recycled into the hydrolysis of fraction c).

18. The process for preparing isophorone according to claim 1, wherein any further phase of fraction b) obtained, composed of products of value is recycled into the reaction.

19. The process for preparing isophorone according to claim 1, wherein the hydrolysis of fraction c) is conducted in a reactive distillation column.

20. The process for preparing isophorone according to claim 19, wherein a water concentration of the hydrolysis is 0.1-99.9% by weight.

21. The process for preparing isophorone according to claim 19, wherein a catalyst concentration is from 0.001-10% by weight.

22. The process for preparing isophorone according to claim 1, wherein the hydrolysis of fraction c) is conducted at least at a pressure of the acetone condensation.

23. The process for preparing isophorone according to claim 1, wherein a temperature of the hydrolysis of fraction c) is 100-300° C.

24. The process for preparing isophorone according to claim 1, wherein the organic fraction d) is purified by distillation.

25. The process for preparing isophorone according to claim 1, wherein the hydrolysis of the residue i) is conducted at a water concentration of 0.1-99.9% by weight.

26. The process for preparing isophorone according to claim 1, wherein a catalyst concentration of the hydrolysis of the residue i) is 0.001-10% by weight.

27. The process for preparing isophorone according to claim 1, wherein a pressure the hydrolysis of the residue i) is 1-200 bar.

28. The process for preparing isophorone according to claim 1, wherein a temperature the hydrolysis of the residue i) is 100-300° C.

29. The process for preparing isophorone according to claim 1, wherein the hydrolysis of the residue i) is conducted in one or more stages in one or more apparatuses.

30. The process for preparing isophorone according to claim 1, wherein the passage of the vapors from the hydrolysis of the residue i) is from the top of the hydrolysis apparatus of residue i) into the hydrolysis of fraction c).

31. The process for preparing isophorone according to claim 1, wherein the hydrolysis of residue i) is conducted in at least one reactive distillation column.

32. The process for preparing isophorone according to claim 1, wherein the hydrolysis of residue i) is conducted in one stage in a reactive distillation column.

33. The process for preparing isophorone according to claim 1, wherein the distillative vapors of fraction e) are passed from the top of the distillative workup apparatus into the hydrolysis of fraction c), the distillative workup of fraction e) being performed in one or more distillation columns.

34. The process for preparing isophorone according to claim 33, wherein wastewater from the bottoms of the distillative work-up of fraction e) (stream f) is sent to a flash evaporation and separated further.

* * * * *